(12) United States Patent
Sheng et al.

(10) Patent No.: US 9,361,712 B2
(45) Date of Patent: Jun. 7, 2016

(54) CT IMAGE GENERATION DEVICE AND METHOD AND CT IMAGE GENERATION SYSTEM

(71) Applicant: Hitachi Medical Corporation, Tokyo (JP)

(72) Inventors: Xingdong Sheng, Beijing (CN); Yingjie Han, Beijing (CN)

(73) Assignee: Hitachi Medical Corporation, Tokyo (JP)

( * ) Notice: Subject to any disclaimer, the term of this patent is extended or adjusted under 35 U.S.C. 154(b) by 97 days.

(21) Appl. No.: 14/381,998

(22) PCT Filed: Jan. 31, 2013

(86) PCT No.: PCT/JP2013/052272
§ 371 (c)(1),
(2) Date: Aug. 29, 2014

(87) PCT Pub. No.: WO2013/132934
PCT Pub. Date: Sep. 12, 2013

(65) Prior Publication Data
US 2015/0010125 A1     Jan. 8, 2015

(30) Foreign Application Priority Data

Mar. 9, 2012 (CN) .......................... 2012 1 0061234

(51) Int. Cl.
*A61B 6/00* (2006.01)
*G06T 11/00* (2006.01)
*A61B 6/03* (2006.01)

(52) U.S. Cl.
CPC ............... *G06T 11/006* (2013.01); *A61B 6/032* (2013.01); *A61B 6/5258* (2013.01); *G06T 2207/10081* (2013.01); *G06T 2207/20041* (2013.01); *G06T 2207/30004* (2013.01); *G06T 2211/424* (2013.01)

(58) Field of Classification Search
CPC ................. A61B 6/032; A61B 6/5258; G06T 2207/20041; G06T 2207/30004; G06T 11/006; G06T 2211/424
USPC .................................. 378/4–20; 382/128–132
See application file for complete search history.

(56) References Cited

U.S. PATENT DOCUMENTS

2003/0194048 A1  10/2003  De Man et al.
2004/0013294 A1   1/2004  Bernard De Man et al.
2010/0119034 A1   5/2010  Hein et al.

FOREIGN PATENT DOCUMENTS

CN          1520783 A        8/2004
CN          1524248 A        8/2004
(Continued)

OTHER PUBLICATIONS

International Search Report from International Application No. PCT/JP13/052272 mailed Jan. 31, 2013.

*Primary Examiner* — Courtney Thomas
(74) *Attorney, Agent, or Firm* — Brundidge & Stanger, P.C.

(57) ABSTRACT

A CT image generation device for analyzing projection information acquired by scanning a scan subject with X-rays over a scan plane, and generating an image of the scan subject; wherein the CT image generation device comprises: a versatile processing unit for establishing a plurality of coordinate systems on the scan plane; a coordinate decision unit for selecting a coordinate system to be used in distance drive back projection or distance drive forward projection, from the plurality of coordinate systems on the basis of a projection angle; a distance drive processing unit for carrying out distance drive back projection or distance drive forward projection on the basis of the selected coordinate system, in accordance with the projection angle; and an image information processing unit for generating the image of the scan subject, on the basis of image information acquired by carrying out distance drive back projection in relation to projection information.

17 Claims, 15 Drawing Sheets

(56) References Cited

FOREIGN PATENT DOCUMENTS

| | | |
|---|---|---|
| DE | 102004004641 A | 8/2004 |
| EP | 1497795 A | 1/2005 |
| JP | 2004-230172 A | 8/2004 |
| JP | 2005-522304 A | 7/2005 |
| JP | 2010-115475 A | 5/2010 |
| NL | 1025371 A | 8/2004 |
| NL | 1025371 C | 2/2006 |
| WO | 03/090170 A1 | 10/2003 |

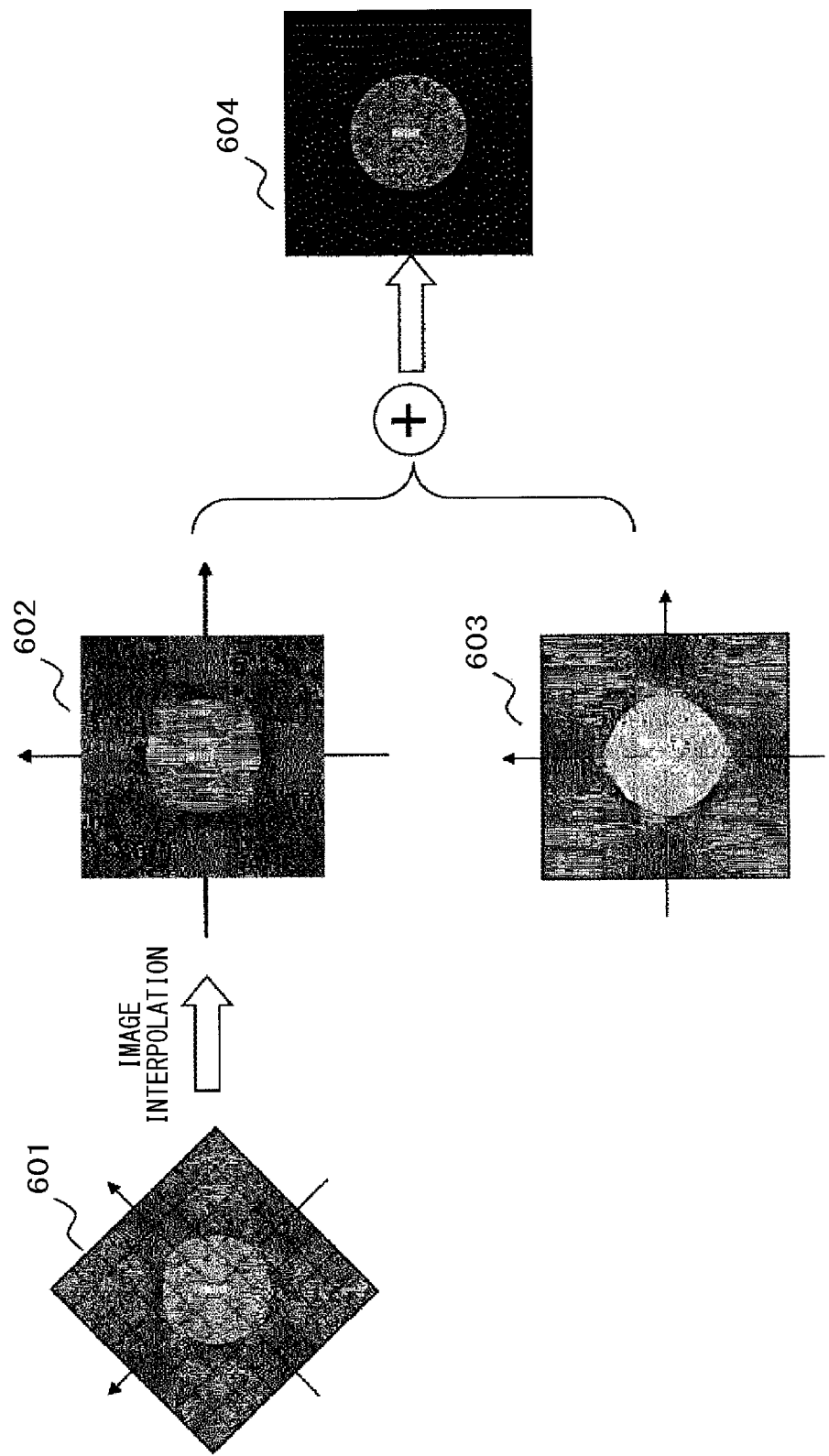

CT IMAGE GENERATION DEVICE AND METHOD AND CT IMAGE GENERATION SYSTEM

TECHNICAL FIELD

The present invention relates to a CT image generation device, a CT image generating method, and a CT image generation system, particularly to a CT image generating method and a CT image generation system that use projection and back projection to reconstruct CT images.

BACKGROUND ART

Technologies of computed tomography (CT) have been broadly used for medical examinations. CT images have been used as bases for disease diagnoses for thirty years. Improvement of CT image quality and reduction of image artifacts (artifacts) are conventional, important issues in studies of CT image reconstruction algorithms and clinics.

Typically, the CT image reconstruction algorithms include a filtered back projection algorithm, an image iterative reconstructive algorithm, and an algebraic image reconstruction algorithm. The filtered back projection algorithm is a main stream of CT image reconstructions, and has been widely used in current CT products. In the filtered back projection algorithm, the filtered back projection is performed to projection data acquired by actual scans to acquire image data.

However, in the filtered back projection algorithm, it is assumed that the projection data for image reconstruction is not affected by noise, but the noise always actually exists in association with the projection data. Since the noise is remarkable particularly in low radiation dose scans, it is difficult to acquire high-definition CT images. However, the clinical application range of CT has spread with development of clinical medical examinations, and CT has reached an extremely higher level than before. Under the background of such a new situation, high image quality is newly desired in consideration of the safety at the time of CT usage in the industry. Therefore, it is difficult for the filtered back projection algorithm to meet the new demand, and the filtered back projection algorithm is used for medium or low level clinical applications in many cases.

The iterative reconstructive algorithm is attracting attention in high-level clinical applications with respect to the above new demand. In the image iterative reconstructive algorithm, image artifacts due to electronic noise and other physical factors are processed properly. Thus, image information can be secured, and radiation dose can be reduced during examinations. However, it was not widely used in actual CT products due to huge calculation amount and high calculation cost. With rapid development of computer technology, the iterative reconstructive algorithm can be applied to the actual products. CT image quality is improved, and image artifacts are reduced, and at the same time, radiation dose necessary for projection can be reduced. With development of medicine and health promotion, the influence of X-ray radiation on human bodies during CT diagnoses is considered more important. Thus, there has been a trend toward low dose CT in the development of CT. Therefore, the iterative reconstructive algorithm has attracted more attention, and is an important subject of research. The iterative reconstructive algorithm mainly includes an iterative projection and back projection process looped multiple times.

In the conventional filtered back projection algorithm, the main process is a back projection process, and when the back projection method such as the conventional pixel-driven type (Pixel-Driven) is used, the model error is large. Therefore, new back projection methods are being studied to reduce artifacts and improve image quality.

On the other hand, in the iterative reconstructive algorithm that has attracted attention, the conventional projection and back projection method based on the ray-driven type (Ray-Driven) and pixel-driven type (Pixel-Driven), the model error is large, and when it is applied to the projection and back projection process in the iterative reconstructive algorithm, it is difficult for the algorithm to converge accurately.

Based on the above situation, many new projection and back projection methods have been studied and proposed, and are used in the conventional filtered back projection algorithm, particularly in the iterative reconstruction algorithm that has attracted attention. The most typical methods include the distance-driven type (Distance-Driven) and separable footprint (Separable Footprint) method. In the distance-driven type, two midline intersections of a pixel block are projection points, and higher model accuracy can be acquired than in the ray-driven type and pixel-driven type.

However, in the distance-driven projection and back projection method, the following technical problem is present. The model error is still large in some angular ranges of the projection/back projection to still affect the image quality after the reconstruction remarkably.

SUMMARY OF THE INVENTION

Technical Problem

Based on the above technical problem in the conventional technology, an object of the present invention is to provide a CT image generation device and method and a CT image generation system in which a model error of projection and back projection can be reduced and which is available also in an iterative reconstructive algorithm and a filtered back projection algorithm to reduce artifacts.

Solution to Problem

For solving the above technical problem in the conventional technology, the present invention provides a CT image generation device. The CT image generation device analyzes projection information acquired by scanning a scan target on a scan plane to generate an image of the scan target, and includes: a general-purpose processing unit that establishes multiple coordinate systems on the scan plane; a coordinate determination unit that selects a coordinate system used in a distance-driven back projection or distance-driven forward projection from the multiple coordinate systems on the basis of a projection angle; a distance-driven processing unit that performs the distance-driven back projection or distance-driven forward projection on the basis of the selected coordinate system in accordance with a projection angle; and an image information processing unit that generates an image of the scan target on the basis of image information acquired by performing the distance-driven back projection to projection information.

The present invention further provides a CT image generation method. The image generation method is a CT image generation method that analyzes projection information acquired by scanning a scan target on the scan plane by use of X-rays to generate an image of the scan target, and includes: a general-purpose processing step for establishing multiple coordinate systems on the scan plane; a coordinate determination step for selecting a coordinate system used in the distance-driven back projection or distance-driven forward projection from the multiple coordinate systems on the basis of a projection angle; a distance-driven processing step for performs the distance-driven back projection or distance-driven forward projection on the basis of the selected coordinate system in accordance with a projection angle; and an image information processing step for generating an image of the scan target on the basis of image information acquired by performing the distance drive back projection to the projection information.

According to the CT image generation device and method of the present invention, a model error in the distance-driven forward projection and back projection of the conventional technology can be reduced by performing the distance-driven forward projection and/or back projection by use of multiple image coordinate systems. Accordingly, reconstruction accuracy of the iterative reconstruction technology and filtered back projection technology is increased, artifacts of CT images are reduced, and an actual CT device and a simulation system of the CT device can be improved.

In the CT image generation device of the present invention, included angles between respective coordinate axes of the multiple coordinate systems established on the scan plane by the general-purpose processing unit may be equal to each other.

In the CT image generation method of the present invention, included angles between respective coordinate axes of the multiple coordinate systems established on the scan plane at the general-purpose processing step may be equal to each other.

According to the above CT image generation device and method, as high accuracy as possible is achievable by a small number of coordinate systems by establishing multiple coordinate systems on the scan plane on the basis of even distribution. Accordingly, the processing load due to combination of coordinate systems can be reduced, and as high CT image reconstruction accuracy as possible is securable.

In the CT image generation device of the present invention, the general-purpose processing unit may establish, on the scan plane, two coordinate systems whose coordinate axes form an included angle of 45 degrees.

In the CT image generation method of the present invention, at the general-purpose processing step, two coordinate systems whose coordinate axes form an included angle of 45 degrees may be established on the scan plane.

According to the above CT image generation device and method, by establishing two coordinate systems on the scan plane on the basis of even distribution, as high accuracy as possible is achievable by a small number of coordinate systems. Accordingly, the processing load due to combination of coordinate systems can be reduced, and high CT image reconstruction accuracy can be securable.

In the CT image generation device of the present invention, the general-purpose processing unit may establish N-number (an integer equal to two or more) of coordinate systems on the scan plane on the basis of an accuracy requirement of the CT image generation device.

In the CT image generation method of the present invention, N-number (an integer equal to two or more) of coordinate systems may be established on the basis of an accuracy requirement of the CT image generation device at the general-purpose processing step.

According to the above CT image generation device and method, the number of coordinate systems is determined based on an accuracy requirement. Accordingly, as few coordinate systems as possible are selected on the premise that an accuracy requirement is met, the processing load due to the combination of coordinate systems is reduced, and required CT image reconstruction accuracy is securable.

In the CT image generation device of the present invention, the coordinate determination unit may select a coordinate system whose coordinate axis and the projection angle form the smallest included angle from the multiple coordinate systems, and the selected coordinate system may be used in the distance-driven back projection or distance-driven forward projection.

In the CT image generation method of the present invention, at the coordinate determination step, a coordinate system whose coordinate axis and the projection angle form the smallest included angle is selected from the multiple coordinate systems, and used in the distance-driven back projection or distance-driven forward projection.

According to the above CT image generation device and method, the coordinate system whose coordinate axis and the projection angle form the smallest included angle is selected. Accordingly, the model error in the distance-driven forward projection and back projection can be minimized.

In the CT image generation device of the present invention, in accordance with each projection angle on the projection plane, the coordinate determination unit selects a coordinate system from the multiple coordinate systems to perform the distance-driven back projection to projection information of the projection angle. On the basis of the coordinate system selected by the coordinate determination unit, the distance-driven processing unit performs the distance-driven back projection to projection information at each projection angle to acquire image information in each coordinate system. The image information processing unit may perform interpolation and addition to the image information in each coordinate system to acquire image information, and may generate an image of the scan target on the basis of the acquired image information.

In the CT image generation method of the present invention, at the coordinate determination step, in accordance with each projection angle on the projection plane, a coordinate system is selected from the multiple coordinate systems to perform the distance-driven back projection to projection information on the projection angle. At the distance-driven processing step, in accordance with the coordinate system selected at the coordinate determination step, the image information in each coordinate system is acquired by performing the distance-driven back projection to the projection information at each projection angle. At the image information processing step, interpolation and addition are performed to the image information in each coordinate system to acquire image information, and an image of the scan target may be generated based on the acquired image information.

According to the above CT image generation device and method, the model error in the distance-driven back projection of the conventional technology can be reduced by performing the distance-driven back projection by use of the multiple image coordinate systems.

In the CT image generation device of the present invention, the image information processing unit performs interpolation to the image information to acquire image information in each coordinate system. In accordance with each projection angle on the projection plane, the coordinate determination unit selects a coordinate system from the multiple coordinate systems to perform the distance-driven forward projection to the image information at the projection angle. On the basis of the coordinate system selected by the coordinate determination unit, the distance-driven processing unit performs the distance-driven forward projection to the image information in the coordinate system at each projection angle to acquire projection information at the projection angle, and may collect the projection information at each projection angle to acquire the projection information.

In the CT image generation method of the present invention, interpolation is performed to image information at the image information processing step to acquire image information in each coordinate system. At the coordinate determination step, in accordance with each projection angle on the projection plane, a coordinate system is selected from the multiple coordinate systems to perform the distance-driven projection to the image information at the projection angle. At the distance-driven processing step, on the basis of the coordinate system selected at the coordinate determination step, the distance-driven forward projection is performed to the image information in the coordinate system at each projection angle to acquire projection information at the projection angle. Then, by collecting the projection information at each projection angle, the projection information may be acquired.

According to the above CT image generation device and method, the model error in the distance-driven projection of the conventional technology can be reduced by performing the distance-driven projection by use of multiple image coordinate systems.

In the CT image generation device of the present invention, the CT image generation device performs at least one iteration of the forward projection and back projection. In the iteration of the forward projection and back projection, the distance-driven forward projection is first performed to the image information acquired using the distance-driven back projection to acquire projection information. After that, the distance-driven back projection may be performed to the projection information acquired using the distance-driven forward projection to acquire image information.

In the CT image generation method of the present invention, at least one iteration of the forward- and back-projection is performed in the CT image generation method. In the iteration of the forward- and back-projection, projection information may be first acquired by performing the distance-driven projection to the image information acquired using the distance-driven back projection. After that, image information may be acquired by performing the distance-driven back projection to the projection information acquired using the distance-driven forward projection.

According to the above CT image generation device and method, the iterative reconstruction including the distance-driven forward projection and back projection is performed using multiple image coordinate systems. Accordingly, a model error in the iterative reconstruction including the distance-driven forward projection and back projection of the conventional technology can be reduced. Accordingly, reconstruction accuracy of the iterative reconstruction technology that has attracted attention in the CT image reconstruction is increased, artifacts of CT images are reduced, and an actual CT device and a simulation system of the CT device can be further improved.

The present invention further provides the CT image generation system. The CT image generation system includes: an X-ray device to scan a scan target by using an X-ray; a detection receiving device to detect and receive projection of the X-ray; a data storage device to store projection information on the received X-ray; and the CT image generation device of the present invention.

According to the CT image generation system of the present invention, the distance-driven forward projection and/or back projection is performed using multiple image coordinate systems. Accordingly, a model error in the distance-driven forward projection and back projection of the conventional technology can be reduced. As a result, the reconstruction accuracy of the iterative reconstruction technology and filtered back projection technology in the CT image reconstruction can be increased, and artifacts of CT images can be reduced.

BRIEF DESCRIPTION OF THE DRAWINGS

FIG. 6 shows an image accumulation principle when two coordinate systems are used;

DETAILED DESCRIPTION OF EMBODIMENTS

Hereafter, based on the figures, specific embodiments of the present invention are described in detail. The specific embodiments are described in detail below for understanding of the contents of the present invention, but do not limit the present invention.

1. Model Error

Figure 1A:
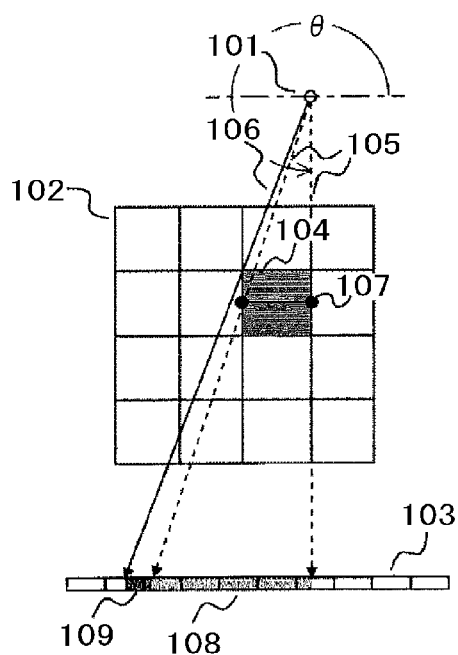
FIG. 1A shows a principle of a distance-driven forward projection and back projection method.
Figure 1B:
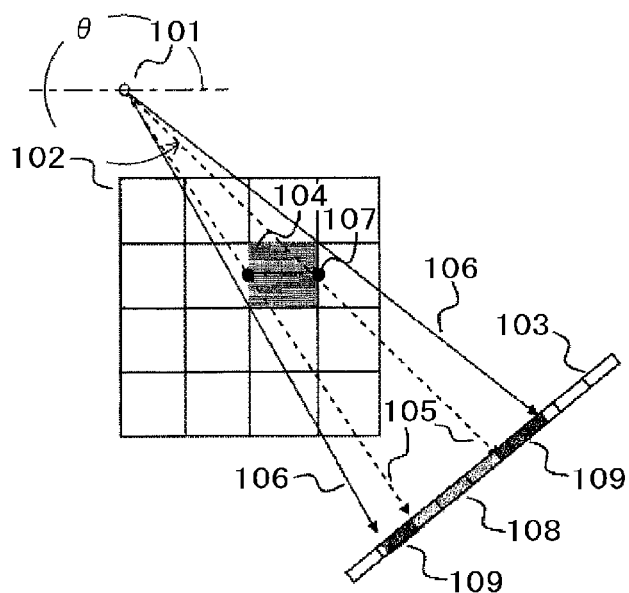
FIG. 1B shows a principle of the distance-driven forward projection and back projection method.
Figure 1C:
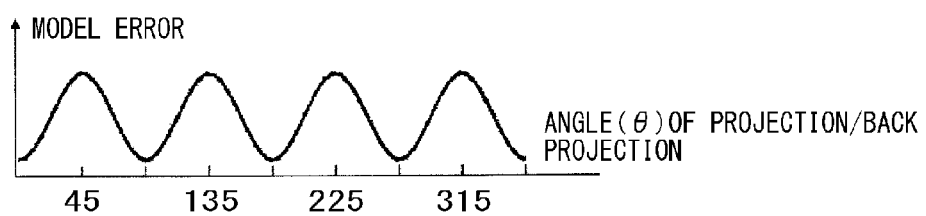
FIG. 1C shows a schematic model error view of the distance-driven forward projection and back projection method.

First, the principle of a distance-driven forward projection and back projection method and its model error are explained. FIG. 1A and FIG. 1B show the principle of the distance-driven forward projection and back projection method. FIG. 1C is a schematic view of a model error of the distance-driven forward projection and back projection method.

As shown in FIG. 1A and FIG. 1B, in the distance-driven forward projection/back projection method, data 108 between two intersections acquired by projecting, to a detector 103, two rays 105 formed by passing two midline intersections 107 of a certain pixel 104 (a pixel shown with a shadowed square in the figure) of an image 102 on a scan plane to scan a scan target from a source point 101 of the forward projection/back projection is data (shown by light shadow in the figure) relating to the pixel 104 in the corresponding detector 103.

However, actually, the data relating to the pixel 104 in the detector 103 further includes 109 (shown by deep shadow in the figure), namely, a detector section between an intersection acquired by projecting, to the detector, a ray 106 passing the outermost of the pixel 104 from the source point 101 of the forward projection/back projection and the side end point of the data 108. Here, 109 is a model error in the distance-driven forward projection/back projection algorithm.

Hereafter, the above model error is analyzed in detail. First, a plane rectangular coordinate system having a coordinate in parallel to a pixel boundary is established. An angle θ formed by the forward projection/back projection direction and the coordinate axis is an angle of the forward projection/back projection (hereinafter may also be generally named a projection angle). Here, a direction of the forward projection/back projection (hereinafter may also be generally named a projection direction) is a direction formed by a ray passing the pixel 104 from the source point 101 as a base point. Since the pixel 104 is actually very small, a specific position where the ray passes the pixel 104 is not limited. For example, the position can be set as a central point passing the pixel 104. When the angle θ of the forward projection/back projection is near 0 degree/90 degrees/180 degrees/270 degrees, the model error is small. On the other hand, the angle θ of the forward projection/back projection is near 45 degrees/135 degrees/225 degrees/315 degrees, the model error is large. FIG. 1C is a schematic model error of the forward projection/back projection to show a relationship between the model error and angle θ of the forward projection/back projection.

The above model error distribution is explained in detail in reference to examples. A plane rectangular coordinate system A is established to have an X axis in the horizontal direction and a Y axis in the vertical direction in FIG. 1A and FIG. 2B. The angle θ formed by a direction of the forward projection/back projection and a positive X-axis direction (set in the right direction in FIG. 1A, and FIG. 1B) is an angle of the forward projection/back projection. For example, the counterclockwise direction from the positive X-axis direction can be positive. When the projection angle is near 270 degrees in the above plane rectangular coordinate system A, FIG. 1A shows that the section 109 is small (in other words, the model error is small). When the projection angle is near 315 degrees in the above rectangular coordinate system A, the section 109 is large (in other words, the model error is large). The model error distribution as shown in FIG. 1C is acquirable in any established plane rectangular coordinate system that has a coordinate axis in parallel to the pixel boundary and that thus is not limited to the above established specific coordinate system.

2. First Embodiment

Hereafter, on the basis of the figures, a CT image generation device and method of the first embodiment of the present invention and a CT image generation system having the CT image generation device are explained in detail.

Figure 2:
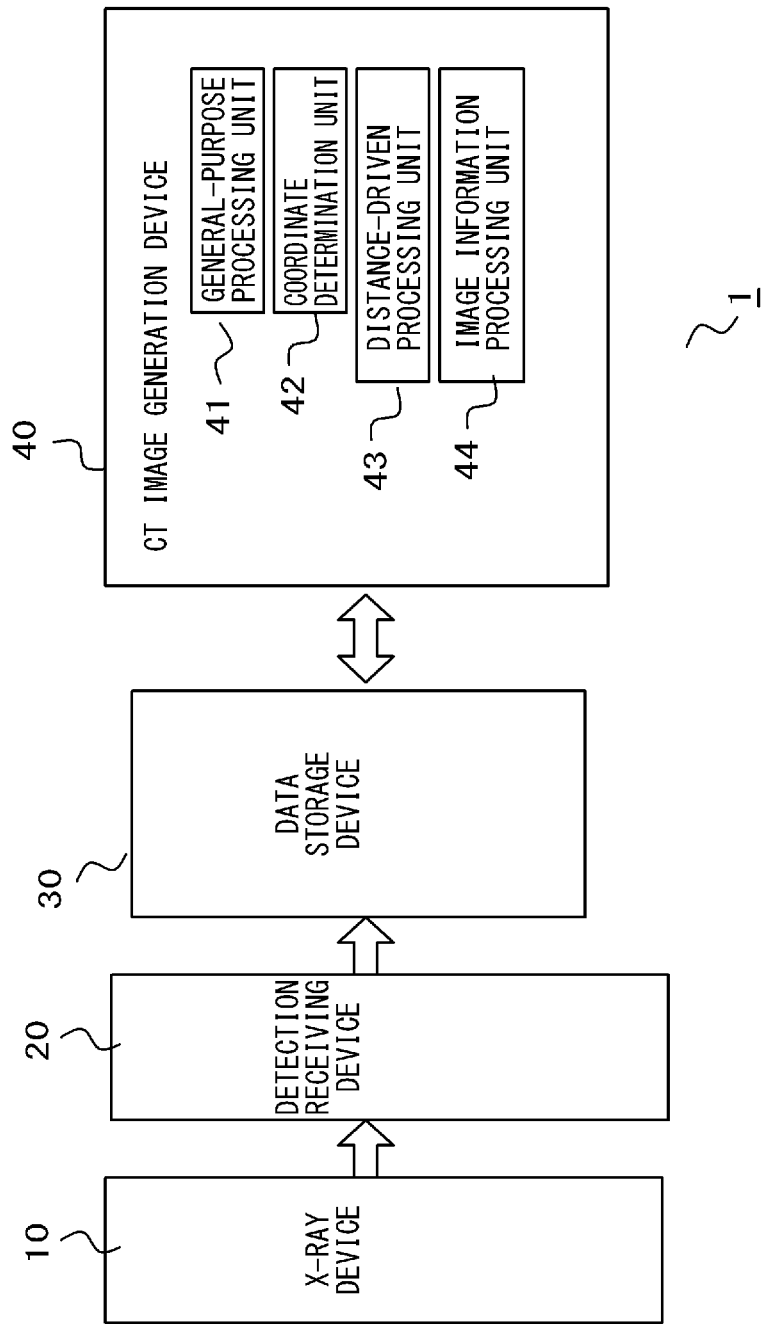
FIG. 2 shows a module showing a configuration of a CT image generation system including a CT image generation device of a first embodiment of the present invention.

2-1. Configuration of CT Image Generation System Having CT Image Generation Device FIG. 2 shows a module showing a configuration of the CT generation system having the CT image generation device of the first embodiment. As shown in FIG. 2, a CT image generation system 1 includes an X-ray device 10, a detection receiving device 20, a data storage device 30, and a CT image generation device 40 of this embodiment.

The X-ray device 10 scans a scan target by using X-rays. The X-ray device 10 is, e.g., an X-ray scanner, and the scan target is, e.g., a human body.

The detection receiving device 20 detects and receives projection of the X-ray. The detection receiving device 20 is, e.g., an X-ray detector (probe), and receives X-ray that is transmitted from the X-ray device 10 and that has scanned a scan target.

The data storage device 30 stores projection information on the received X-ray. The data storage device 30 is realized by a ROM, RAM, HDD, memory card, etc.

The CT image generation device 40 of this embodiment analyzes projection information acquired by scanning a scan target on a scan plane by using the X-ray to generate an image of the scan target. The CT image generation device 40 is realized by a computer, single chip microcomputer, CPU, MPU, integrated circuit, etc.

2-2. Characteristics Module of CT Image Generation Device

Hereafter, subsequently, based on FIG. 2, a characteristics module of the CT image generation device 40 of this embodiment is explained.

The CT image generation device 40 of this embodiment operates as a specific function unit such as the general-purpose processing unit 41, coordinate determination unit 42, distance-driven processing unit 43, and image information processing unit 44 by making a processor execute a predetermined program. Naturally, the CT image generation device 40 of this embodiment is realizable not only by this but also by an integrated circuit by use of, e.g., FPGA.

2-2-1. General-Purpose Processing Unit

The general-purpose processing unit 41 establishes multiple coordinate systems on a scan plane. In this embodiment, establishing of two coordinate systems is explained. Establishing of three or more coordinates is explained later.

Figure 3A:
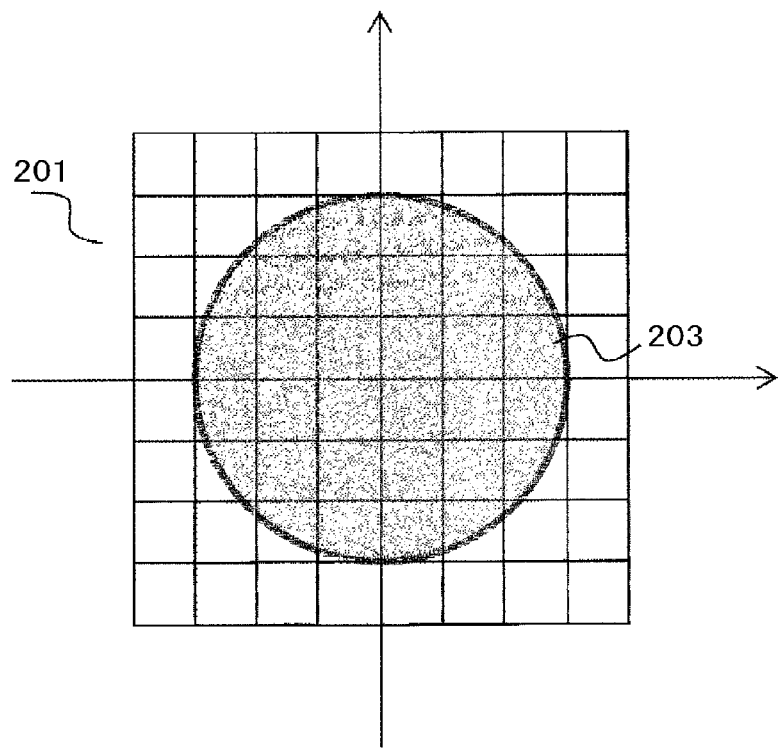
FIG. 3A is a schematic view of each coordinate system when two coordinate systems are used.
Figure 3B:
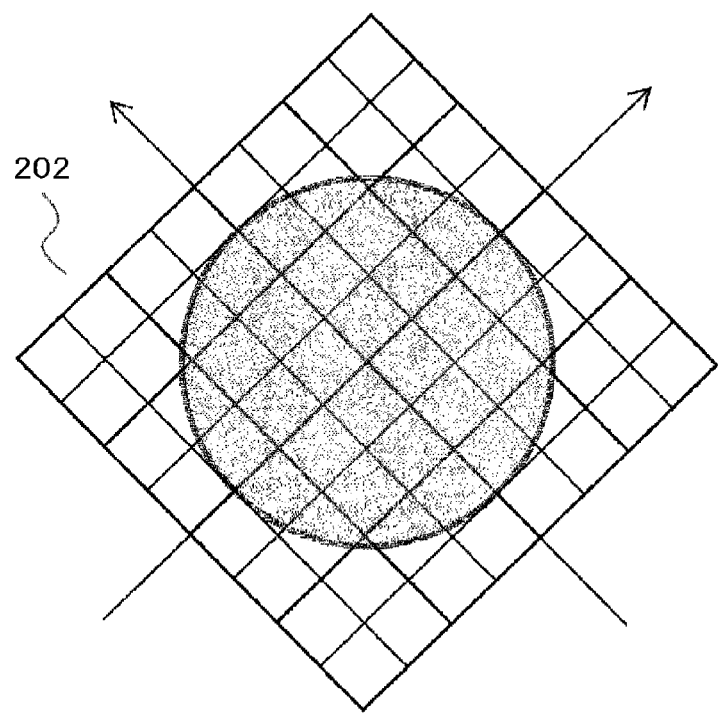
FIG. 3B is a schematic view of each coordinate system when two coordinate systems are used.

FIG. 3A and FIG. 3B are schematic views of respective coordinate systems when two coordinate systems are used. FIG. 3A shows a coordinate system 201 that is the same as the plane rectangular coordinate system A established in the above sentence. Hereafter, such a coordinate system is called a reference coordinate system. FIG. 3B shows a coordinate system 202 acquired by rotating the reference coordinate system shown in FIG. 3A to a predetermined angle. Hereafter, such a coordinate system is called a rotation coordinate system. Here, the reference coordinate system and the rotation coordinate system are arbitrarily determined for easy explanation, and are equivalent. In the figures, a section 203 shown by shadow shows a section of an active reconstruction image.

As shown in FIG. 3A and FIG. 3B, each included angle between coordinate axes of respective two coordinate systems established by the general-purpose processing unit 41 on the scan plane is the same as each other, 45 degrees. Namely, a rotation angle of the rotation coordinate system relative to the reference coordinate system is 45 degrees (the counterclockwise direction is positive). Based on the principle of even distribution, two coordinate systems are established within the scan plane (360 degrees). As a result, high accuracy is achieved by as few coordinate systems as possible, the processing load brought by combining coordinate systems with each other is reduced, and high CT image reconstruction accuracy is securable. Naturally, the rotation angle of the rotation coordinate system relative to the reference coordinate system may be other than 45 degrees, and may be any angle selected from angles over 0 degree and under 90 degrees.

2-2-2. Coordinate Determination Unit

The coordinate determination unit 42 selects a coordinate system for the distance-driven back projection or distance-driven forward projection from multiple coordinate systems established by the general-purpose processing unit 41 on the basis of a projection angle. In this embodiment, the situation of selecting from two coordinate systems is explained, and the situation of selecting from three or more coordinate systems is explained later.

Figure 4:
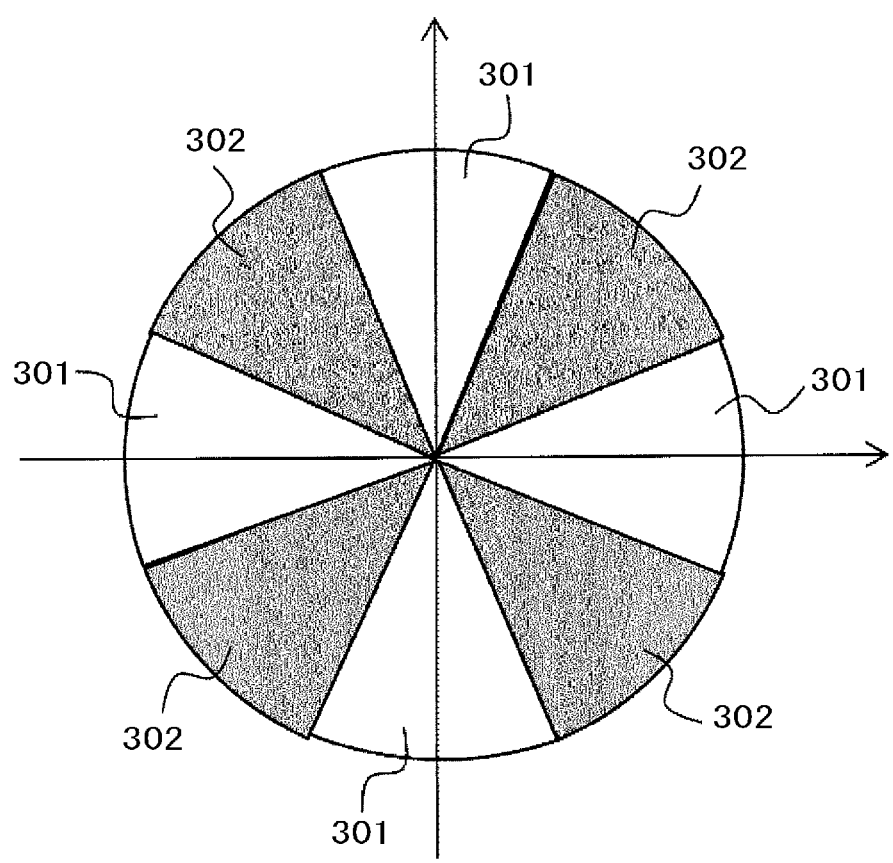
FIG. 4 is a schematic view of selecting a coordinate system on the basis of a projection angle when two coordinate systems are used.

FIG. 4 is a schematic view of selecting a coordinate system on the basis of a projection angle in case in which two coordinate systems are used. As shown in FIG. 4, the reference coordinate system 201 is used for the forward projection/back projection within the angular range shown by 301, and the rotation coordinate system 202 is used for the forward projection/back projection within the angular range shown by 302.

The coordinate determination unit 42 selects a coordinate system whose certain coordinate axis and a projection angle form the smallest included angle from the coordinate systems 201 and 202, and by use of the selected coordinate system, the distance-driven back projection or distance-driven forward projection is performed at the projection angle. As a result, the model error in the distance-driven forward projection and back projection can be minimized.

2-2-3. Distance-Driven Processing Unit

The distance-driven processing unit 43 performs the distance-driven back projection or distance-driven forward projection on the basis of the coordinate system selected by the coordinate determination unit 42 in accordance with a projection angle.

In the distance-driven back projection, based on the coordinate system selected by the coordinate determination unit 42, the distance-driven processing unit 43 performs the distance-driven forward projection to projection information at each projection angle to acquire image information in each coordinate system. In the distance-driven forward projection, based on the coordinate system selected by the coordinate determination unit 42, the distance-driven processing unit 43 performs the distance-driven forward projection to the image information in each coordinate system corresponding to each projection angle to acquire the projection information at the projection angle.

2-2-4. Image Information Processing Unit

The image information processing unit 44 generates an image of the scan target based on the image information acquired by performing the distance-driven back projection to the projection information.

In the distance-driven back projection, the image information processing unit 44 acquires image information by performing interpolation and addition to the image information in each coordinate system acquired by the distance-driven back projection performed by the distance-driven processing unit 43. Additionally, in the distance-driven forward projection, the image information processing unit 44 performs interpolation to the image information to acquire image information in each coordinate system established by the general-purpose processing unit 41.

Figure 5A:
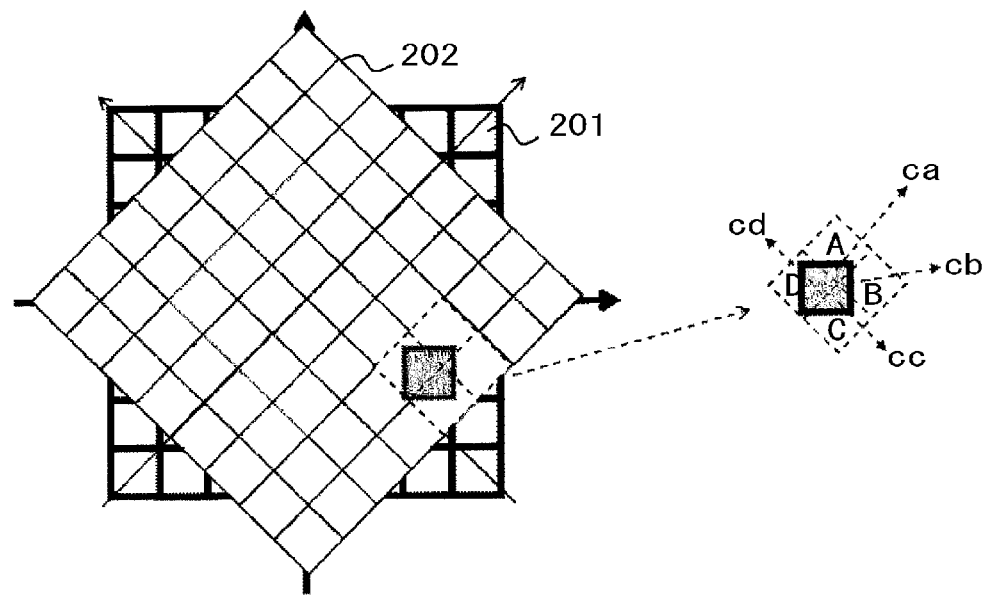
FIG. 5A shows an interpolation principle when two coordinate systems are used.
Figure 5B:
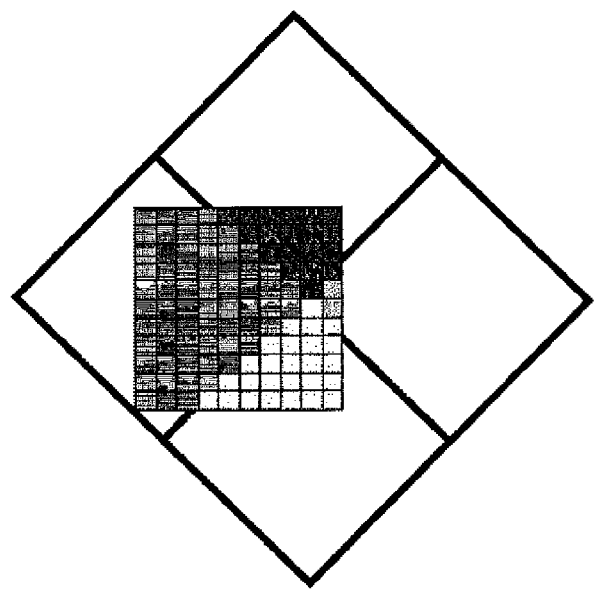
FIG. 5B shows an interpolation principle when two coordinate systems are used.

Hereafter, the interpolation performed by the image information processing unit 44 is explained specifically. FIG. 5A and FIG. 5B shows the interpolation principle when two coordinate systems are used. The image interpolation between multiple coordinate systems (two herein) is calculated by areas occupied by pixels between the coordinate systems. FIG. 5A shows a specific method of performing interpolation calculation of pixels of the rotation coordinate system 202, and acquiring a pixel in the reference coordinate system 201. By calculating a ratio relationship (area ratio) of areas of overlapping sections between a certain pixel of the determined reference coordinate system and pixels of the rotation coordinate system, each covered pixel in the rotation coordinate system is weighted and accumulated by using this area ratio. For example, a pixel value C(x, y) of a pixel x, y) (shown by shadow in the figure) of the reference coordinate system 201, the pixel being acquired by the interpolation to the rotation coordinate system 202, is calculable by Formula 1.

$$C(x,y)=ca \times A+cb \times B+cc \times C+cd \times D \quad (1)$$

In Formula 1, ca, cb, cc, and cd, as shown in the figure, show occupation ratios of the areas (pixel overlapping section areas) of the overlapping sections between the pixel (x, y) in the reference coordinate system and the pixel A, pixel B, pixel C, and pixel D in the rotation coordinate system relative to the pixel area, namely pixel overlapping section area ratios. In Formula, A, B, C, and D show pixel values of the pixel A, pixel B, pixel C, and pixel D in the rotation coordinate system, respectively.

The same method is used also when the interpolation calculation of the reference coordinate system is performed to the rotation coordinate system. In the back projection, it is necessary to perform the interpolation calculation of an image of each rotation coordinate system to the reference coordinate system. In the projection, it is necessary to perform the interpolation calculation of an image of the reference coordinate system to each rotation coordinate system.

FIG. 5B shows a specific example of calculating the overlapping section area ratio. By defining the pixel block in the reference coordinate system into smaller blocks, the number of blocks in the pixels in the rotation coordinate system are summed to show area ratios of the overlapping sections. In the embodiment, the interpolation relationships and interpolation coefficients of the pixels, i.e., the area ratios are calculated in advance by a processor and stored in the storage device.

Hereafter, subsequently, processing of the image information processing unit 44 is explained. FIG. 6 shows an image accumulation principle when two coordinate systems are used. In this embodiment, the situation of accumulating two coordinate systems is explained, and is similar to the situation of accumulating three or more coordinate systems. As mentioned above, in the back projection, respective angles are distributed over the different coordinate systems to perform the back projection and to generate back projection images in multiple coordinate systems (two systems herein). After the interpolation of an image 601 in the rotation coordinate system 202 on the reference coordinate system through the above interpolation method, an interpolation image 602 is acquired. Further, the interpolation image 602 is accumulated with an image 603 in the reference coordinate system 201 to acquire a final result image, i.e., an image 604 of a scan target.

2-3. Process of CT Image Generation Method

Hereafter, based on the figures, the CT image generation method of this embodiment is explained. The CT image generation method of this embodiment analyzes the projection information acquired by scanning a scan target on the scan plane by using X-rays, and generates an image of the scan target.

Figure 7:
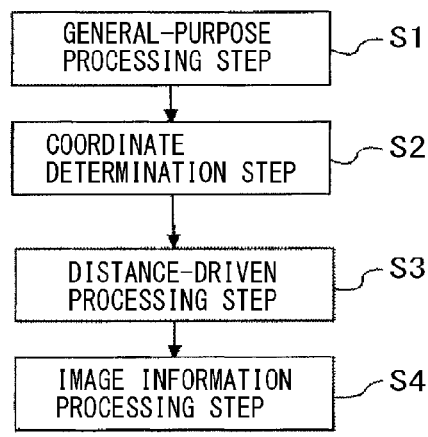
FIG. 7 shows a flowchart showing a CT image generation method of the first embodiment.

FIG. 7 is a flowchart of the CT image generation method of the first embodiment. As shown in FIG. 7, the CT image generation method of this embodiment includes: a general-purpose processing step S1 for establishing multiple coordinate systems on the scan plane; a coordinate determination step S2 for selecting a coordinate system used for the distance-driven back projection or distance-driven forward projection from multiple coordinate systems established at the general-purpose processing step S1 on the basis of a projection angle; a distance-driven processing step S3 of performing the distance-driven back projection or distance-driven projection on the basis of the coordinate system selected at the coordinate determination step S2 in accordance with a projection angle; and an image information processing step S4 for generating an image of a scan target on the basis of the image information acquired by performing the distance-driven back projection to the projection information at the distance-driven processing step S3.

2-4. Advantageous Effect of First Embodiment

Hereafter, based on the figures, an advantageous effect of this embodiment is explained in detail.

Figure 8A:
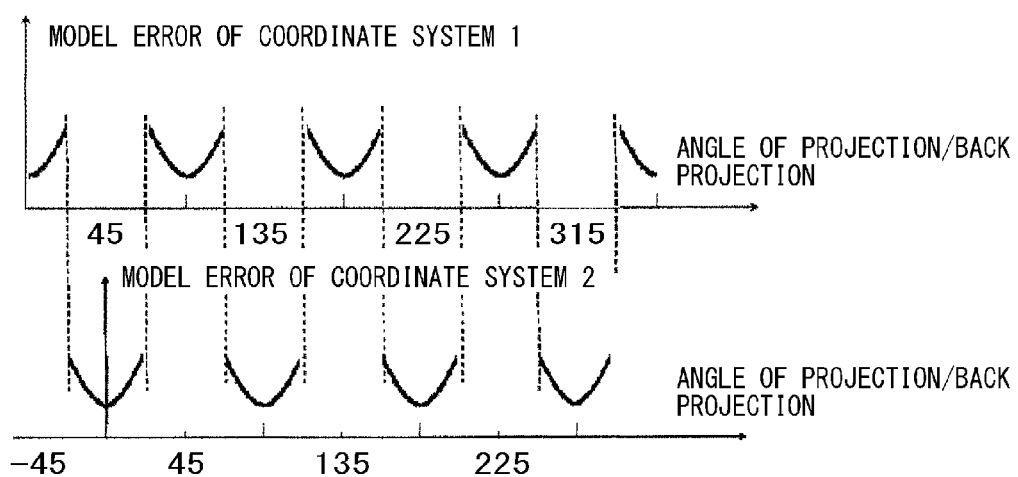
FIG. 8A shows a model error reduction principle when two coordinate systems are used.
Figure 8B:
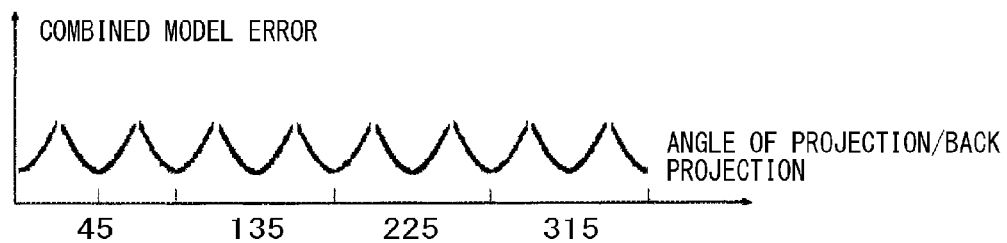
FIG. 8B shows a model error reduction principle when two coordinate systems are used.

FIG. 8A and FIG. 8B show the model error reduction principle when two coordinate systems are used. In FIG. 8A and FIG. 8B, the horizontal axis shows an angle of the forward projection/back projection, and the vertical axis shows a model error.

When a different coordinate system is selected in response to a different angle of the forward projection/back projection as shown in FIG. 8A, the largest model error portions (near 45 degrees/135 degrees/225 degrees/315 degrees) in the single coordinate system shown in FIG. 1C are deleted. The model error in the coordinate system corresponding to each projection angle is reduced. Accordingly, as shown in FIG. 8B, the overall combined model error after the results of the forward projection/back projection at respective angles are combined is obviously reduced in comparison with the distance-driven model error in the single coordinate system in FIG. 1C, and a low model error is maintained even at each forward projection/back projection angle.

As mentioned above, according to the CT image generation device and method of the present invention, the model error in the distance-driven forward projection and back projection of the conventional technology can be reduced by performing the distance-driven forward projection and/or back projection by use of multiple image-coordinates systems. As a result, the iterative reconstruction technology in the CT image reconstruction and the reconstruction accuracy of the filtered back projection technology can be enhanced, artifacts of CT images can be reduced, and an actual CT device and the simulation system of the CT device can be improved.

3. Second Embodiment

The second embodiment of the present invention reduces a model error further and increases the reconstruction accuracy by using three or more coordinate systems on the basis of the first embodiment. Hereinafter, differences of the second embodiment from the first embodiment are explained, but the same or similar points as or to the first embodiment are not explained.

3-1. Features of Second Embodiment

3-1-1. Establishment of Coordinate Systems

According to a technical proposal of the present invention, with the increase in coordinate systems, the portions with large errors are reduced, and the combined model error becomes smaller as the number of coordinate systems is larger. However, in the actual execution, since combination calculations increase as the number of coordinate systems is larger, the number of coordinate systems is selectable based on this embodiment.

In this embodiment, the general-purpose processing unit 41 establishes N number of coordinate systems (N is an integer equal to two or more) on the scan plane on the basis of an accuracy requirement of the CT image generation device 40 or CT image generation system 1. At the general-purpose processing step S1, N number of coordinate systems (N is an integer equal to two or more) are established on the scan plane on the basis of an accuracy requirement of the CT image generation method. As a result, the number of coordinate systems is determined based on the accuracy requirement, and as few coordinate systems as possible are selected on the assumption that the accuracy requirement is met, so that the processing load due to the combination of the coordinate systems can be reduced, and the required CT image reconstruction accuracy is securable.

Figure 9A:
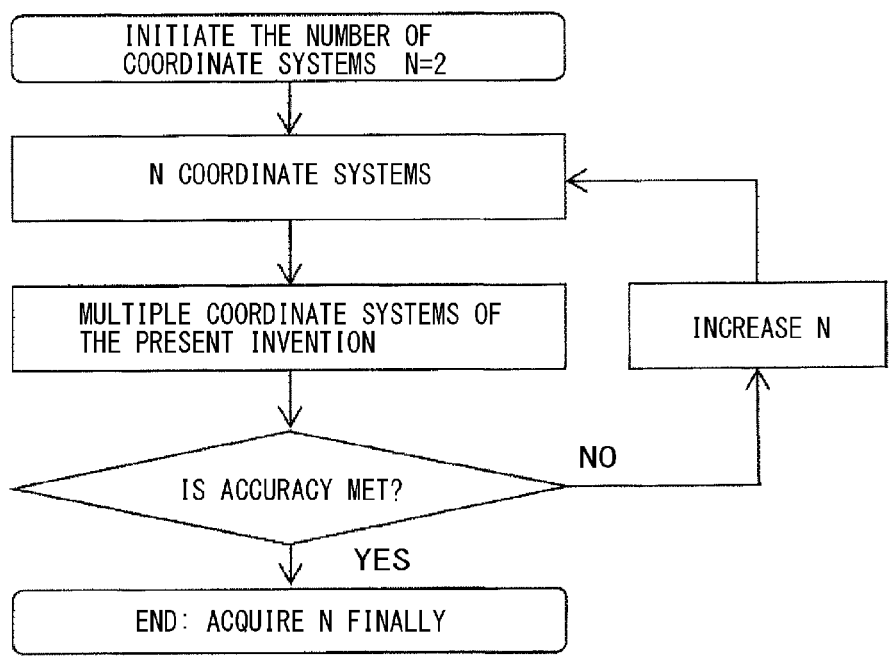
FIG. 9A shows a flowchart showing establishment of multiple coordinate systems in the second embodiment of the present invention.
Figure 9B:
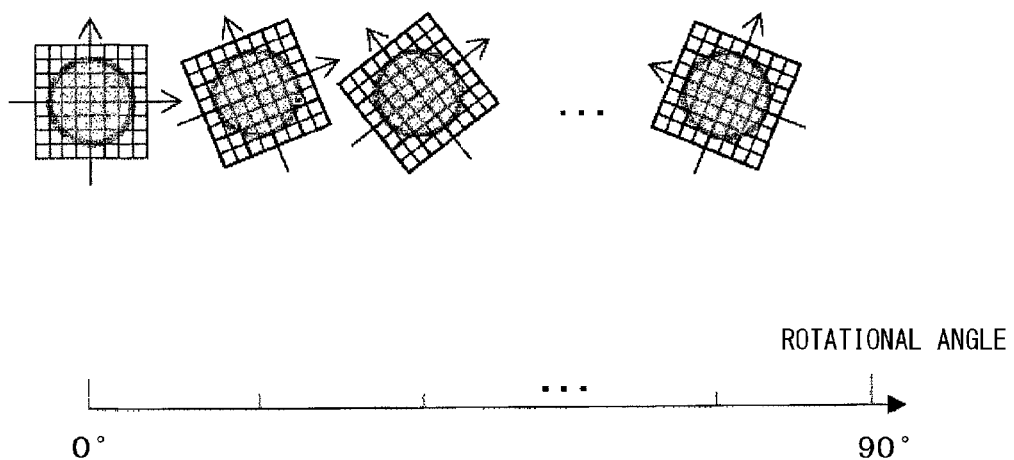
FIG. 9B shows a schematic view showing a rotational angle of each coordinate system when multiple coordinate systems are used.

FIG. 9A is a flowchart showing establishment of multiple coordinate systems in the second embodiment. FIG. 9B is a schematic view showing a rotation angle of each coordinate system when multiple coordinate systems are established. The process of establishing multiple coordinate systems in FIG. 9A is based on the following ideas. In other words, in embodiment, the selection of the number of coordinate systems may use two coordinate systems first, and the number of coordinate systems may be increased until an accuracy requirement is met when it is difficult for two coordinate systems to meet the accuracy requirement. In execution, it is recommended that the number of the coordinate systems be set to the power of two. Part of the calculation time for the result data of the projection and back projection performed in the reference image coordinate system 201 after the increase in the number of the coordinate systems can be saved by repeatedly using the former calculation results.

In the method for selecting a rotation angle of the coordinate system, when the number K of selected coordinate systems is larger than two, X-axis rotational angles of K−1 number of coordinate systems (the second and following coordinate systems in the figure) are optimally distributed within 0 to 90 degrees as shown in FIG. 9B. Naturally, other angles may be selected separately, but the rotation angles of K−1 number of coordinate systems must not be the same.

That is, included angles between respective coordinate axes of multiple coordinate systems established on the scan plane may be equal to each other. In accordance with the principle of even distribution, multiple coordinate systems are established within the scan plane (360 degrees). As a result, as high accuracy as possible is achieved using the small number of coordinate systems, the processing load due to the combination of the coordinate systems is reduced, and as high CT image reconstruction accuracy as possible is securable. Naturally, the included angles between respective coordinate axes of multiple coordinate systems established on the scan plane may be any angle except 0 degree, and different from each other.

In the explanation of the above specific example, examination is performed since the time of establishing two coordinate systems until the number of coordinate systems is acquired to meet the accuracy requirement. When the number of the coordinate systems has been known to meet the accuracy requirement, the number of the coordinate systems may be determined directly, naturally.

3-1-2. Selection of Coordinate System

Similarly to the case where two coordinate systems are used, the coordinate determination unit 42 selects a coordinate system whose coordinate axis and a projection angle form the smallest included angle from multiple coordinate systems, and the selected coordinate system is used for the distance-driven forward projection or distance-driven back projection. As a result, the model error in the distance-driven forward projection and back projection can be minimized.

3-2. Case where Three Coordinate Systems are Present

As a representative case where three or more coordinate systems are used, the case where three coordinate systems are used is explained in detail based on the figures hereafter.

The cases where the other numbers of coordinate systems are used are similar to each other, and not explained here.

Figure 10A:
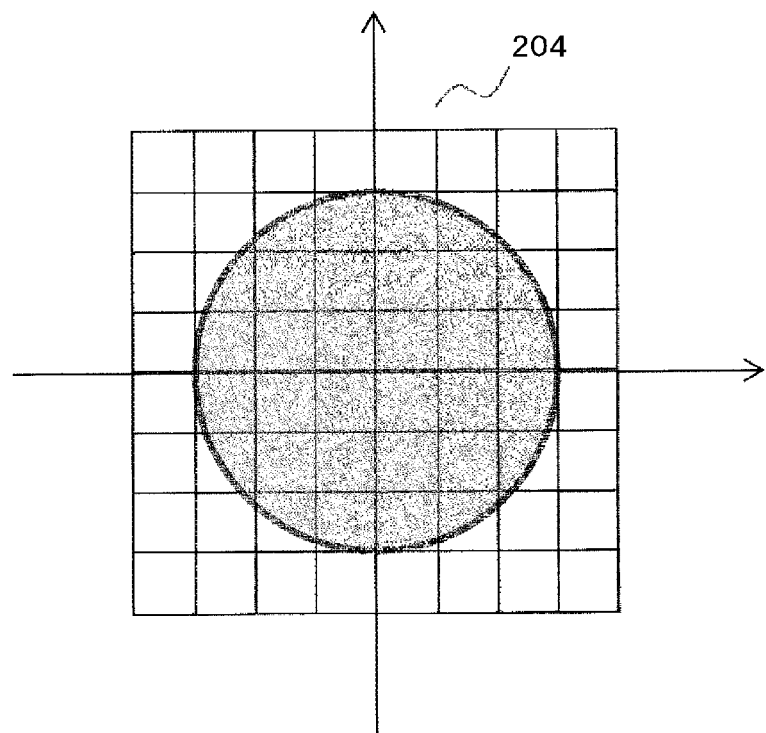
FIG. 10A shows a schematic view of each coordinate system when three coordinate systems are used.
Figure 10B:
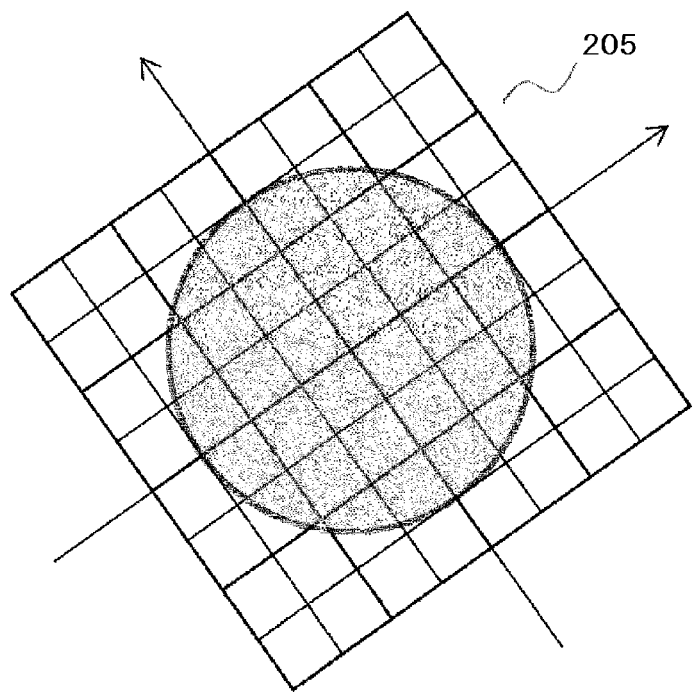
FIG. 10B shows a schematic view of each coordinate system when three coordinate systems are used.
Figure 10C:
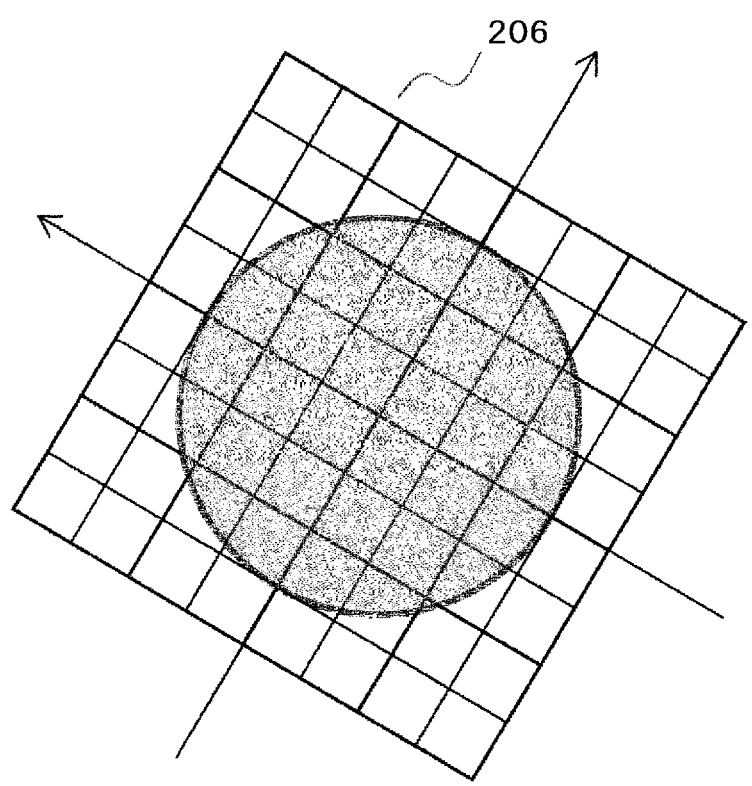
FIG. 10C shows a schematic view of each coordinate system when three coordinate systems are used.

FIGS. 10A, 10B, and 10C are schematic views of respective coordinate systems in the case where three coordinate systems are present. FIG. 10A shows a reference coordinate system 204. FIG. 10B shows a rotation coordinate system 205 acquired by rotating the reference coordinate system by 30 degrees (counterclockwise rotation is positive). FIG. 10C shows a rotation coordinate system 206 acquired by rotating the reference coordinate system by 60 degrees (counterclockwise rotation is positive).

Figure 11:
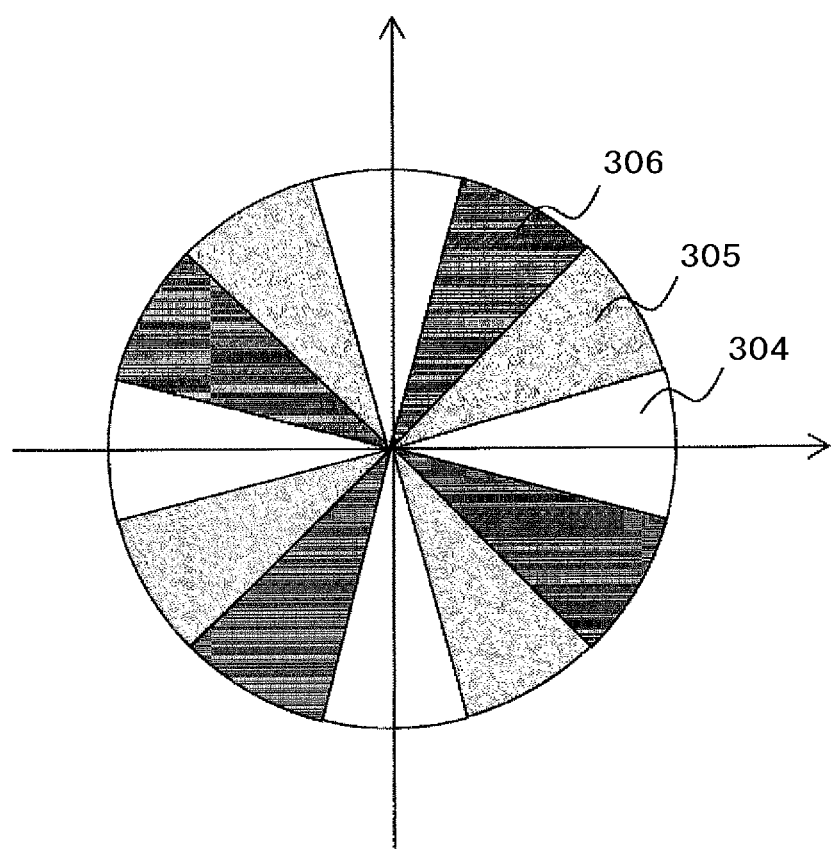
FIG. 11 shows a schematic view of selecting a coordinate system on the basis of a projection angle when three coordinate systems are used.

FIG. 11 is a schematic view to select a coordinate system based on a projection angle in the case where the number of coordinate systems is three. This case is similar to the case where two coordinate systems are used. A coordinate system whose coordinate axis and the projection angle form the smallest included angle is selected from three coordinate systems for use in the distance-driven back projection or distance-driven forward projection. As shown in FIG. 11, angle ranges corresponding to 304, 305, and 306 use the coordinate systems 204, 205, and 206, respectively.

Figure 12A:
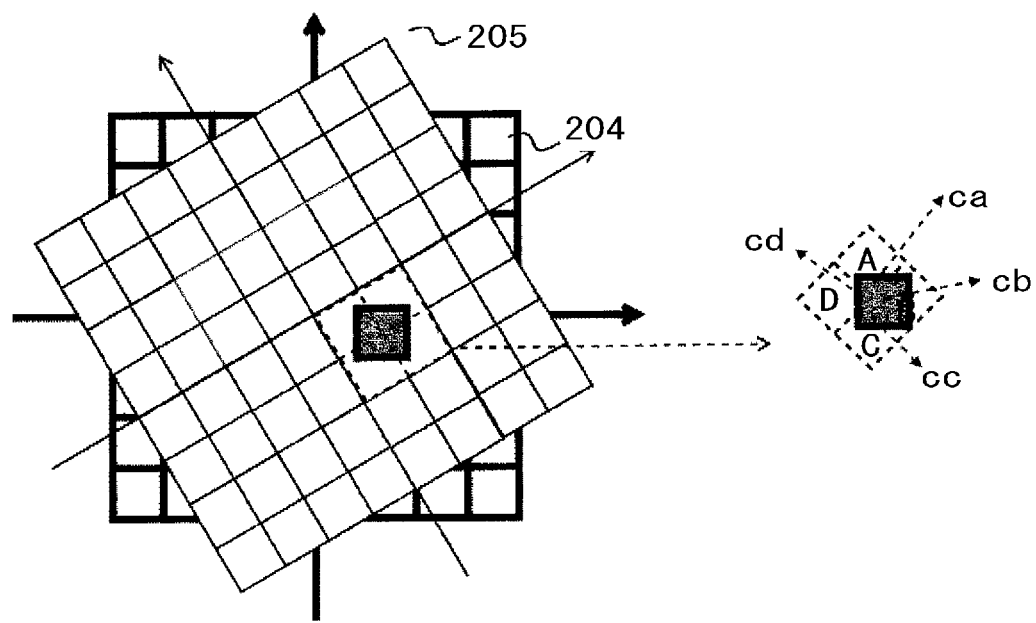
FIG. 12A shows an interpolation principle when three coordinate systems are used.
Figure 12B:
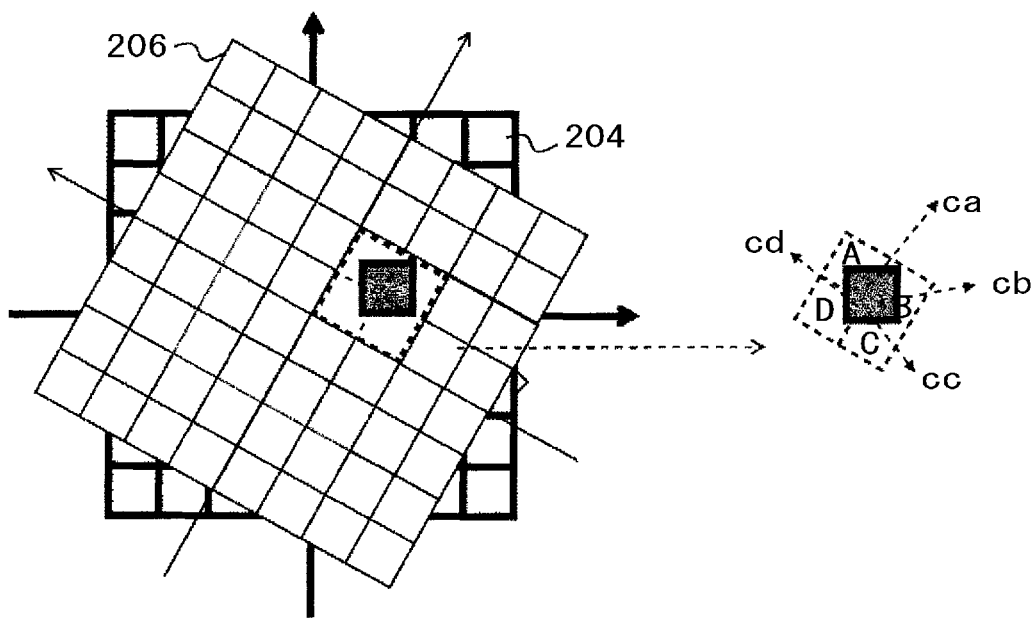
FIG. 12B shows an interpolation principle when three coordinate systems are used.

FIG. 12A and FIG. 12B are interpolation principle views in the case where three coordinate systems are used.

Similarly to the case where two coordinate systems are used, a pixel value $C_{21}(x, y)$ of a pixel $(x, y)$ of the reference coordinate system 204 (shown by shadow in the figure) acquired by the interpolation to the rotation coordinate system 205 can be calculated by Formula 2, as shown in FIG. 12A.

$$C_{21}(x,y)=ca \times A+cb \times B+cc \times C+cd \times D \quad (2)$$

As shown in FIG. 12B, a pixel value $C_{22}(x, y)$ of a pixel $(x, y)$ of the reference coordinate system 204 (shown by shadow in the figure) acquired by the interpolation to the rotation coordinate system 206 can be calculated by Formula 3.

$$C_{22}(x,y)=ca \times A+cb \times B+cc \times C+cd \times D \quad (3)$$

As shown in the figure, ca, cb, cc, and cd in Formula show ratios of image overlapping section areas of the pixel $(x, y)$ in the reference coordinate system and the pixel A, pixel B, pixel C, and pixel D in the rotation coordinate system relative to the pixel area, namely pixel overlapping section area ratios. In Formula, A, B, C, and D show pixel values of the pixel A, pixel B, pixel C, and pixel D in the rotation coordinate system, respectively.

Similarly to the case where two coordinate systems are used, when three coordinate systems are used, the result after the interpolation of the coordinate system 205 and coordinate system 206 and the image of the coordinate system 204 are accumulated in the distance-driven back projection to acquire a final reconstruction image. For example, an accumulation value $I_m(x, y)$ can be calculated by Formula 4.

$$I_m(x,y)=C_1(x,y)+C_{21}(x,y)+C_{22}(x,y) \quad (4)$$

$C_1(x, y)$ is reconstruction image data of the coordinate system 204, and $C_{21}(x, y)$ and $C_{22}(x, y)$ are image data in which the coordinate system 2 and coordinate system 3 are respectively interpolated to the coordinate system 1.

Figure 13A:
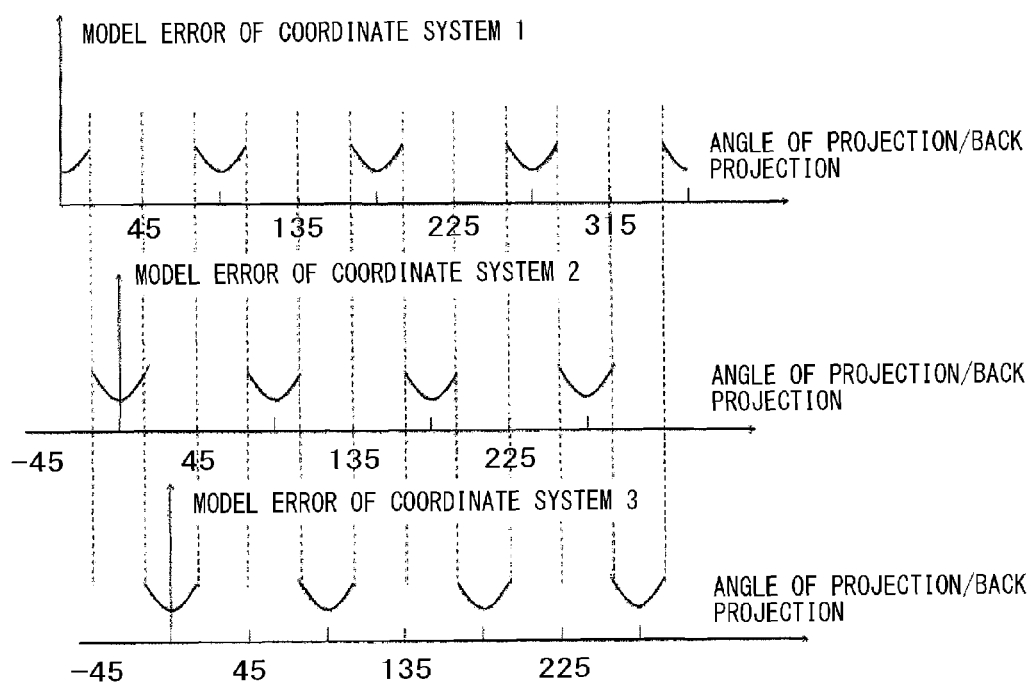
FIG. 13A shows a model error reduction principle when three coordinate systems are used.
Figure 13B:
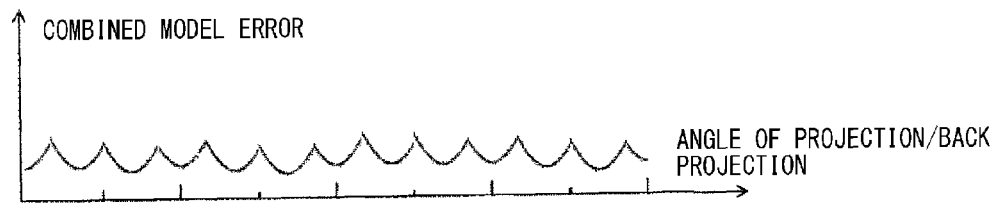
FIG. 13B shows a model error reduction principle when three coordinate systems are used.

FIG. 13A and FIG. 13B show a model error reduction principle when three coordinate systems are used. In FIG. 13A and FIG. 13B, the horizontal axis shows an angle of the forward projection/back projection, and the vertical axis shows a model error. As shown in FIG. 13A and FIG. 13B, when three coordinate systems are selected for different angles of the forward projection/back projection, the overall combined model error after the results of respective forward projections/back projections are combined is obviously reduced relative to the distance-driven model error in the single coordinate system in FIG. 1C, and simultaneously further reduced relative to the distance-driven model error in the two coordinate systems shown in FIG. 8B. The distance-driven model error is maintained low in each angle of the forward projection/back projection.

4. Third Embodiment

In the third embodiment of the present invention, the first and second embodiments are applied to the filtered back projection and iterative reconstruction in the CT image reconstruction. Hereafter, differences of the third embodiment from the first and second embodiments are mainly explained. The same or similar points as or to the first and second embodiments are not explained.

4-1. Filtered Back Projection

In the back projection, the back projections in different angles are calculated in different coordinate systems, and finally, image results in different coordinate systems are interpolated, and accumulated to final image information.

When the present invention is applied to the filtered back projection of the CT image reconstruction, the coordinate determination unit 42 selects a coordinate system from multiple coordinate systems established by the general-purpose processing unit 41 to perform the distance-driven back projection to projection information of each projection angle on the projection plane in accordance with the projection angle, the distance-driven processing unit 43 acquires image information in each coordinate system by performing the distance-driven back projection to projection information of each projection angle in accordance with the coordinate system selected by the coordinate determination unit 42, and the image information processing unit 44 performs interpolation and addition to image information in each coordinate system to acquire image information, and generates an image of a scan target on the basis of acquired image information.

When the present invention is applied to the filtered back projection of the CT image reconstruction, the following steps are performed. In the coordinate determination step S2, in accordance with each projection angle on the projection plane, a coordinate system is selected from multiple coordinate systems established at the general-purpose processing step S1 to perform the distance-driven back projection to projection information at the projection angle. In the distance-driven processing step S3, on the basis of the coordinate system selected in the coordinate determination step 2, the distance-driven back projection is performed to projection information at each projection angle to acquire image information in each coordinate system. In the image information processing step 4, interpolation and addition is performed to the image information in each coordinate system to acquire image information, and on the basis of the acquired image information, an image of the scan target is generated.

Figure 14:
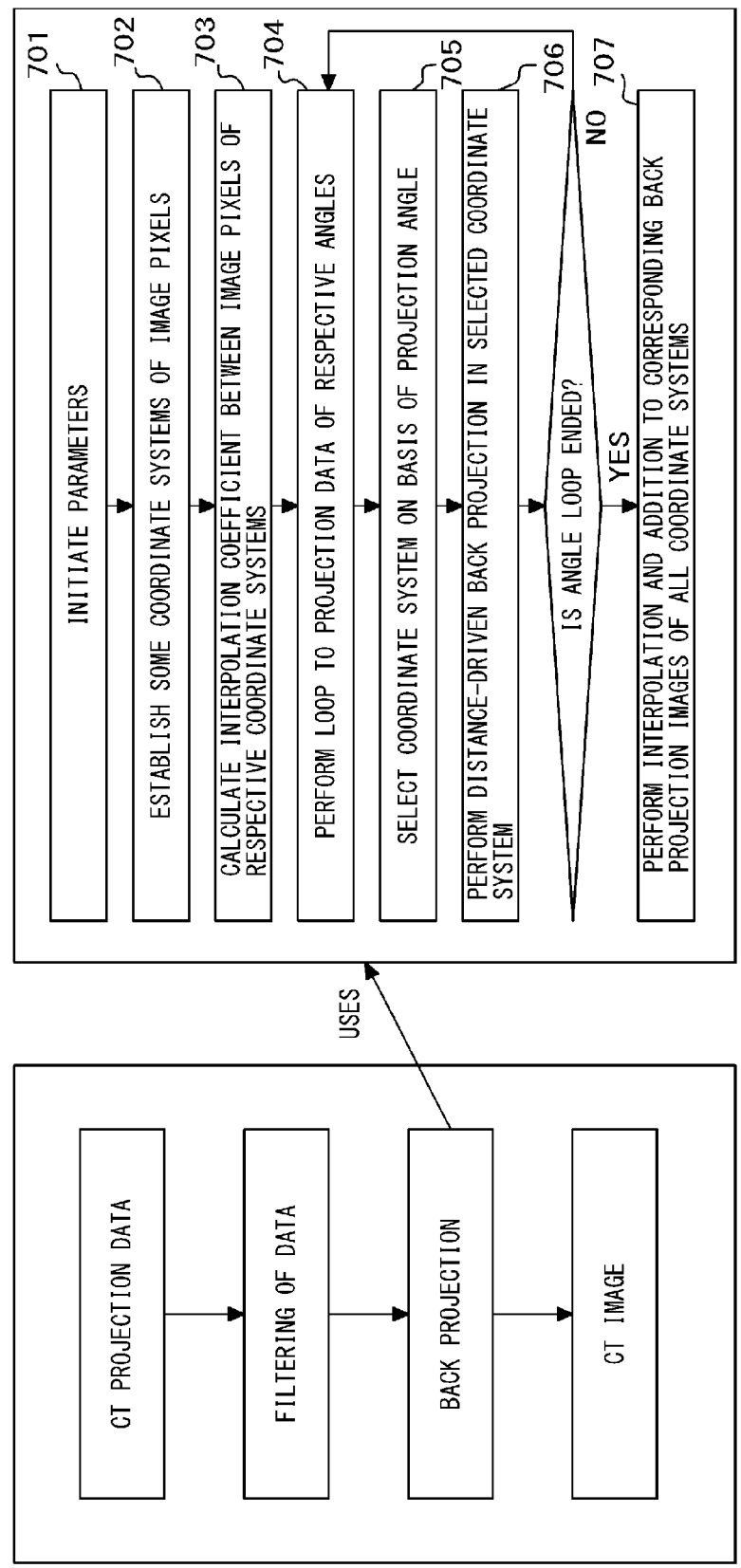
FIG. 14 shows a flowchart showing a filtered back projection of a third embodiment of the present invention.

Hereafter, a specific example of the present invention applied to filtered back projection is explained based on the figures. FIG. 14 is a flowchart of the filtered back projection processing of the third embodiment. As shown in FIG. 14, first, data filtering is performed to CT projection data (projection information), and after that, the back projection is performed. Then, based on a result of the back projection, a CT image is generated. In the back projection, parameters such as the number of coordinate systems and rotation angles are initialized at Step 701. At Step 702, coordinate systems are established based on the parameters, and an initially reset image corresponding to each coordinate system is set. At Step 703, an interpolation coefficient between an image pixel in each rotation coordinate system and an image pixel in the reference coordinate system is calculated. At Step 705, a coordinate system whose coordinate axis and a projection angle form the smallest included angle is selected to be a coordinate system for the back projection of the data at the projection angle. At Step 706, the back projection is performed in the selected coordinate system, and its result is accumulated in the image corresponding to the selected coordinate system. At Step 707, interpolation calculations of corresponding back projection images in all the coordinate systems are performed for accumulation in the image in the reference coordinate system.

In the specific example of the above filtered back projection, Step 702 corresponds to the general-purpose processing step S1 of the present invention, Step 705 corresponds to the coordinate determination step S2 of the present invention, Step 706 corresponds to the distance-driven processing step S3 of the present invention, and Step 707 corresponds to the image information processing step S4 of the present invention. The respective steps in the specific example are applied to a specific modification of the filtered back projection, and be adjustable and changeable in their order in accordance with an actual situation.

As mentioned above, the present invention is applied to the filtered back projection in the CT image reconstruction. Accordingly, the model error in the distance-driven back projection of the conventional technology is reduced, and reconstruction accuracy of the filtered back projection technology in the CT image reconstruction is increased. Consequently, artifacts of CT images are reduced, and actual CT devices and simulation systems of CT devices can be improved.

4-2. Iterative Reconstruction

When the present invention is applied to the iterative reconstruction of the CT image reconstruction, after the distance-driven back projection is performed as mentioned above, accuracy of the reconstruction is increased by performing further at least one iteration of the forward- and back-projections. In the iteration of the forward- and back-projections, projection information is acquired by first performing the distance-driven forward projection to the image information acquired by the distance-driven back projection. After that, image information is acquired by performing distance-driven back projection to the image information acquired by the distance-driven forward projection.

The back projection has been already explained. In the forward projection, an image for projection is first calculated by interpolation, and mapped to different coordinate systems. Further, based on a projection angle, the images in the different coordinate systems are selected and projected to collect projection data at all the angles and to then generate final projection data.

When the distance-driven projection is performed to the image information acquired by the distance-driven back projection, the image information processing unit 44 performs interpolation to the image information. Then, image information in each coordinate system is acquired. The coordinate determination unit 42 selects a coordinate system from multiple coordinate systems established by the general-purpose processing unit 41 to perform the distance-driven projection to the image information at each projection angle in accordance with the projection angle. The distance-driven processing unit 43, on the basis of the coordinate system selected by the coordinate determination unit 42, performs the distance-driven projection to the image information in the coordinate system at each projection angle to acquire image information at the projection angle, and collects projection information at each projection angle to acquire the projection information.

When the distance-driven forward projection is performed to the image information acquired by the distance-driven back projection, the following steps are performed. Interpolation is performed to the image information at the image information processing step S4 to acquire image information in each coordinate system. At the coordinate determination step S2, in accordance with each projection angle on the projection plane, a coordinate system is selected from the multiple coordinate systems established at the general-purpose processing step S1 to perform the distance-driven forward projection to the image information at the projection angle. At the distance-driven processing step S3, on the basis of the coordinate system selected at the coordinate determination step S2, the distance-driven forward projection is performed to the image information in the coordinate system at each projection angle to acquire projection information at the projection angle, and the projection information at each projection angle is collected to acquire projection information.

Hereinafter, on the basis of the figures, a specific example in which the present invention is applied to the iterative reconstruction, and a specific example of projection in the iterative reconstruction is mainly explained.

Figure 15:
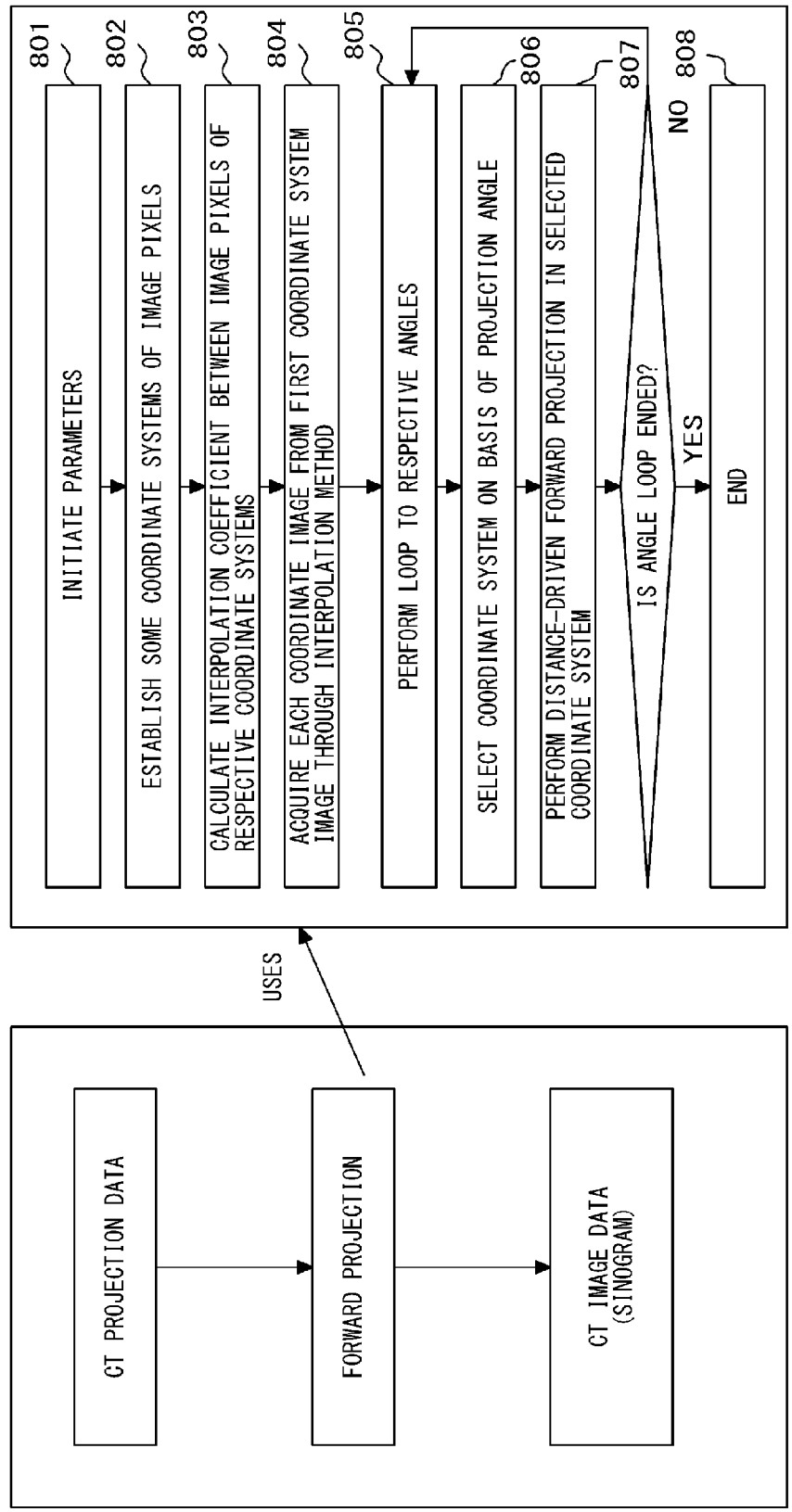
FIG. 15 shows a flowchart showing a projection of the third embodiment.

FIG. 15 is a flowchart showing projection processing of the third embodiment. As shown in FIG. 15, in projection processing, CT projection data (projection information) is generated by performing the forward projection (projection) to CT image data (image information). Specifically, at Step 801, parameters such as the number of coordinate systems and rotation angles are initialized. At Step 802, coordinate systems are established based on the parameters and an image corresponding to each coordinate system is installed. At Step 803, an interpolation coefficient between an image pixel in each coordinate system and an image pixel in the reference coordinate system is calculated. At Step 804, by use of the interpolation method, an image of each coordinate system is acquired from an initial image, in other words, an image in each coordinate system is acquired by interpolating the input image in the reference coordinate system. At Step 806, a coordinate system is selected based on a projection angle, and the coordinate system whose coordinate axis and the projection angle form the smallest included angle is a coordinate system for the forward projection at the angle. At Step 807, in the selected coordinate system, the distance-driven forward projection is performed. At Step 808, the processing ends.

In the specific example of the above projection, Step 802 corresponds to the general-purpose processing step S1 of the present invention, Step 806 corresponds to the coordinate determination step S2 of the present invention, Step 807 corresponds to the distance-driven processing step S3 of the present invention, and Step 804 corresponds to the image information processing step S4 of the present invention. Each step in the specific example is applicable to a specific modification of projection, and the order thereof is adjustable and changeable in accordance with an actual situation.

By performing the distance-driven projection by use of multiple image coordinate systems as mentioned above, the model error in the distance-driven projection of the conventional technology can be reduced. Further, by performing the iterative reconstruction including the distance-driven forward projection and back projection by use of multiple image coordinate systems, the model error in the iterative reconstruction including the distance-driven forward projection and back projection of the conventional technology can be reduced. Accordingly, the reconstruction accuracy of the iterative reconstruction technology that has attracted attention in the CT image reconstruction is increased. Further, artifacts are reduced to further improve actual CT devices and simulation systems of the CT devices.

5. Supplement

As mentioned above, some embodiments and examples of the present invention have been described in detail. The present invention is not limited to these. Further various modifications, combinations, and deletions are possible within the spirit of the present invention. The embodiments acquired by modifications, combinations, and deletions are also contained within the present invention.

For example, parameters and data of the present invention (for example, projection information, image information, etc.) can be stored in the form such as sinograms (Sinogram) that store and manage projection data, coordinate systems and interpolation coefficients that store and manage coordinate system parameters (numbers, rotation angles, etc.) and interpolation coefficients between coordinate system image pixels, an each-coordinate-system correspondence images that store and manage images corresponding to each coordinate system, and input/output result images that store and manage input (to projection)/output (to back projection) result images.

For example, the CT image generation system 1 of the present invention may further include a user interface module that provides a data interface for display, an image printer, etc. Accordingly, a user can easily acquire data such as an image of a scan target, the image being generated from the CT image generation device 40 or CT image generation system 1 of the present invention.

The invention claimed is:

1. A CT image generation device that analyzes projection information acquired by scanning a scan target on a scan plane by using X-rays to generate an image of the scan target, the device comprising:
a general-purpose processing unit that establishes a plurality of coordinate systems on the scan plane;
a coordinate determination unit that selects a coordinate system used in a distance-driven back projection or a distance-driven forward projection from the multiple coordinate systems in accordance with a projection angle;
a distance-driven processing unit that performs a distance-driven back projection or a distance-driven forward projection on a basis of the selected coordinate system in accordance with a projection angle, and
an image information processing unit that generates an image of the scan target on a basis of image information acquired by performing a distance-driven back projection to projection information.

2. The CT image generation device according to claim 1, wherein included angles between respective coordinate axes of the multiple coordinate systems established on the scan plane by the general-purpose processing unit are equal to each other.

3. The CT image generation device according to claim 1, wherein the general-purpose processing unit establishes two coordinate systems on the scan plane, and an included angle between respective coordinate axes of the two coordinate systems is 45 degrees.

4. The CT image generation device according to claim 1, wherein the general-purpose processing unit establishes N number of coordinate systems (N is an integer equal to two or more) on a scan plane in accordance with an accuracy requirement of the CT image generation device.

5. The CT image generation device according to claim 1, wherein the coordinate determination unit selects a coordinate system whose coordinate axis and the projection angle form a smallest included angle from the plurality of coordinate systems, and the selected coordinate system is used in a distance-driven back projection or a distance-driven forward projection.

6. The CT image generation device according to claim 1,
wherein the coordinate determination unit, in accordance with each projection angle on a projection plane, selects a coordinate system from the plurality of coordinate systems to perform a distance-driven back projection,
the distance-driven processing unit, on a basis of a coordinate system selected by the coordinate determination unit, performs a distance-driven back projection to projection information at each projection angle to acquire image information in each coordinate system, and the image information processing unit acquires image information by performing interpolation and addition to image information in each coordinate system, and generates an image of the scan target on a basis of acquired image information.

7. The CT image generation device according to claim 1, wherein the image information processing unit acquires image information in each coordinate system by performing interpolation to image information, the coordinate determination unit, in accordance with each projection angle on the projection plane, selects a coordinate system from the plurality of coordinate systems to perform a distance-driven forward projection to image information at the projection angle, and the distance-driven processing unit, in accordance with a coordinate system selected by the coordinate determination unit, performs a distance-driven forward projection to image information in the coordinate system at each projection angle to acquire projection information at the projection angle, and collects projection information at each projection angle to acquire projection information.

8. The CT image generation device according to claim 1, wherein at least one iteration of forward and back projections is performed, and in the iteration of the forward and back projections, a distance-driven forward projection is first performed to image information acquired using a distance-driven back projection to acquire projection information, and after that, a distance-driven back projection is performed to the projection information acquired using a forward projection to acquire image information.

9. A CT image generation device comprising:
an X-ray device to scan a scan target by using an X-ray;
a detection receiving device to detect and receive projection of the X-ray;
a data storage device to store projection information on the received X-ray; and
the CT image generation device of claim 1.

10. A CT image generation method for analyzing projection information acquired by scanning a scan target on a scan plane by use of X-rays to generate an image of the scan target, the method comprising:
a general-purpose processing step for establishing a plurality of coordinate systems on a scan plane;
a coordinate determination step for selecting a coordinate system used in a distance-driven back projection or a distance-driven forward projection from the plurality of coordinate systems on a basis of a projection angle;
a distance-driven processing step for performing a distance-driven back projection or a distance-driven forward projection on a basis of a selected coordinate system in accordance with the projection angle; and
an image information processing step for generating an image of the scan target on a basis of image information acquired by performing a distance-driven back projection to projection information.

11. The CT image generation method according to claim 10, wherein included angles between respective coordinate axes of the plurality of coordinate systems are equal to each other.

12. The CT image generation method according to claim 10, wherein, at the general-purpose processing step, two coordinate systems are established on the scan plane, and an included angle between respective coordinate axes of the two coordinate systems is 45 degrees.

13. The CT image generation method according to claim 10, wherein, at the general-purpose processing step, on a basis of an accuracy requirement of the CT image generation method, N number of coordinate systems (N is an integer equal to two or more) are established on a scan plane.

14. The CT image generation method according to claim 10, wherein, at the coordinate determination step, a coordinate system whose coordinate axis and the projection angle form a smallest included angle is selected from the plurality of coordinate systems, and used in a distance-driven back projection or a distance-driven forward projection.

15. The CT image generation method according to claim 10,
wherein at the coordinate determination step, in accordance with each projection angle on the projection plane, a coordinate system is selected from the plurality of coordinate systems to perform a distance-driven back projection to projection information at the projection angle,
at the distance-driven processing step, a distance-driven back projection is performed to projection information at each projection angle to acquire image information at each projection angle on a basis of a coordinate system selected at the coordinate determination step, and
at the image information processing step, interpolation and addition is performed to image information in each coordinate system to acquire image information, and an image of the scan target is generated on a basis of acquired image information.

16. The CT image generation method according to claim 10,
wherein at the image information processing step, image information in each coordinate system is acquired by performing interpolation to image information,
at the coordinate determination step, in accordance with each projection angle on the projection plane, a coordinate system is selected from the plurality of coordinate systems to perform a distance-driven forward projection to image information at the projection angle, and
at the distance-driven processing step, on a basis of a coordinate system selected at the coordinate determination step, a distance-driven forward projection is performed to image information in the coordinate system at each projection angle to acquire projection information at the projection angle, and projection information at each projection angle is collected to acquire projection information.

17. The CT image generation method according to claim 10, wherein at least one iteration of a projection and back projection is performed, and in an iteration of the forward and back projections, a distance-driven forward projection is first performed to image information acquired using a distance-driven back projection, and after that, a distance-driven back projection is performed to the projection information acquired using the forward projection to acquire image information.

* * * * *